(12) United States Patent
Edmondson et al.

(10) Patent No.: US 9,936,937 B2
(45) Date of Patent: Apr. 10, 2018

(54) SURGICAL RETRACTOR

(71) Applicant: Brigham Young University, Provo, UT (US)

(72) Inventors: Bryce Edmondson, Provo, UT (US); Quentin Allen, Lindon, UT (US); Michael McCain, Provo, UT (US); John J. Pierce, Provo, UT (US); Terri Bateman, American Fork, UT (US); Larry Howell, Orem, UT (US)

(73) Assignee: Brigham Young University, Provo, UT (US)

( * ) Notice: Subject to any disclaimer, the term of this patent is extended or adjusted under 35 U.S.C. 154(b) by 668 days.

(21) Appl. No.: 14/464,512

(22) Filed: Aug. 20, 2014

(65) Prior Publication Data

US 2015/0065805 A1 Mar. 5, 2015

Related U.S. Application Data

(60) Provisional application No. 61/868,062, filed on Aug. 20, 2013.

(51) Int. Cl.
*A61B 17/02* (2006.01)
*A61B 1/32* (2006.01)
*A61B 17/00* (2006.01)

(52) U.S. Cl.
CPC ............ *A61B 17/0218* (2013.01); *A61B 1/32* (2013.01); *A61B 17/02* (2013.01); *A61B 17/0206* (2013.01); *A61B 2017/00004* (2013.01); *A61B 2017/00849* (2013.01); *A61B 2017/00862* (2013.01); *A61B 2017/0225* (2013.01)

(58) Field of Classification Search
CPC . A61B 1/32; A61B 2017/00862; A61B 17/02; A61B 17/0206; A61B 17/0218; A61B 2017/0225
See application file for complete search history.

(56) References Cited

U.S. PATENT DOCUMENTS 5,339,803 A * 8/1994 Mayzels ............ A61B 17/0218
600/201
5,351,679 A * 10/1994 Mayzels ............ A61B 17/0218
600/214

(Continued)

OTHER PUBLICATIONS

International Search Report for International Patent Application No. PCT/US2014/051927, dated Dec. 17, 2014.

*Primary Examiner* — Larry E Waggle, Jr.
(74) *Attorney, Agent, or Firm* — Sean D. Detweiler, Esq.; Morse, Barnes-Brown & Pendleton, P.C.

(57) ABSTRACT

A surgical retractor device for retaining and/or moving internal organs during minimally invasive or laparoscopic surgery is provided. The surgical retractor can be a single continuous structure that includes a shaft. The shaft can branch into a first elongate finger with a first distal end opposite the shaft and a second elongate finger with a second distal end opposite the shaft. The retractor can further include a resilient lattice structure disposed between the first elongate finger and the second elongate finger. The retractor can have an expanded configuration and a collapsed configuration based on relative distance between the first distal end and the second distal end. When the retractor is in the collapsed configuration, spring force energy can be stored in the resilient lattice structure.

21 Claims, 7 Drawing Sheets

(56) References Cited

U.S. PATENT DOCUMENTS

| | | |
|---|---|---|
| 5,439,476 A | 8/1995 | Frantzides |
| 5,904,649 A * | 5/1999 | Andrese ............. A61B 17/0218 600/204 |
| 6,248,062 B1 | 6/2001 | Adler et al. |
| 7,322,935 B2 | 1/2008 | Palmer et al. |
| 8,313,507 B2 | 11/2012 | Ravikumar |
| 8,517,931 B2 | 8/2013 | Minnelli et al. |
| 2011/0105848 A1 | 5/2011 | Sadovsky et al. |
| 2012/0123215 A1 | 5/2012 | Begg |
| 2012/0303112 A1 | 11/2012 | Armstrong et al. |

* cited by examiner

SURGICAL RETRACTOR

RELATED APPLICATION(S)

This application claims priority to, and the benefit of, U.S. Provisional Application 61/868,062, filed Aug. 20, 2013, for all subject matter common to both applications. The disclosure of said provisional application is hereby incorporated by reference in its entirety.

GOVERNMENT FUNDING

This invention was made with government support under NSF Grant No. 1240417 awarded by the National Science Foundation and Air Force Office of Scientific Research. The government has certain rights in the invention.

FIELD OF THE INVENTION

The present invention relates to a surgical retraction instrument suitable for use in laparoscopic surgery. In particular, the present invention relates to a surgical retractor that is capable of retaining and/or moving internal organs during laparoscopic or minimally invasive surgery.

BACKGROUND

Generally, laparoscopic surgery is performed by making a small incision in the body and placing a cannula through the incision to the area to be operated on. The surgical instruments are then inserted through the cannula and manipulated from outside the body. During these procedures, the surgeon is often required to expose and handle delicate tissues, organs and other structures within the body. To accomplish this, the surgeon uses a retractor device. Such retractor devices are generally inserted into the body cavity in a collapsed configuration and are guided to their intended target. Once the retractor reaches the intended target, the retractor is expanded. The expanded configuration enables the retractor to move and/or retain organs or other structures within the body. Examples of commonly-performed laparoscopic surgical operations include endoscopic appendectomy and laparoscopic cholecystectomy.

However, the use of surgical retractor devices during laparoscopic or minimally invasive surgery experiences some shortcomings. Traditional retractors may lack the ability to properly grip or cup organs, which may be soft, slippery, and comprise a variety of shapes. They may also be incapable of applying the required forces needed to move larger organs without bending or deforming. Furthermore, traditional retractors are often difficult to insert through a small space, expand, and then compress smoothly and quickly. In addition, some traditional retractors are unsafe due to their sharp edges, which can cause scrapes, punctures, or other injuries within the body, thereby limiting the situations where such retractors can be used. Conventional laparoscopic retractors may also be difficult to clean because of their many small grooves and spaces. Likewise, the manufacture of conventional retractors can involve numerous steps, tools, processes, and assembly scenarios, because of the many small mechanical parts used to create the joints or hinges of the retractors.

SUMMARY

There is a need for developing a retractor with improved grip, improved manufacturability, improved rigidity, improved compliance, improved functionality, and improved safety. The present invention is directed toward further solutions to address this need, in addition to having other desirable characteristics.

In accordance with an example embodiment of the present invention, a surgical retractor is provided. The surgical retractor can be a single continuous structure that includes a shaft. The shaft can branch into a first elongate finger with a first distal end opposite the shaft and a second elongate finger with a second distal end opposite the shaft. The retractor can further include a resilient lattice structure disposed between the first elongate finger and the second elongate finger. The retractor can have an expanded configuration and a collapsed configuration based on relative distance between the first distal end and the second distal end. When the retractor is in the collapsed configuration, spring force energy can be stored in the resilient lattice structure.

In accordance with aspects of the present invention, the shaft can have a diameter ranging from about 1 mm to about 12 mm (about 0.04 inches to about 0.47 inches) and a length ranging from about 51 mm to about 610 mm (about 2 inches to about 24 inches). The retractor can be formed from a biocompatible material. Each of the first and second elongate fingers can be straight. The first and second elongate fingers can be in the collapsed configuration when the retractor is introduced into a body cavity. The first and second elongate fingers can have substantially the same degree of flexibility. The resilient lattice structure can be folded when the retractor is introduced into a body cavity. The resilient lattice structure can have a diamond-shaped pattern or a semi-circular pattern. The retractor can form an angle between 0 degrees and 90 degrees, with an open position set anywhere in that range, between the first and second elongate fingers. For example, the retractor can form a 90 degree angle, a 45 degree angle, or a 12 degree angle, between the first and second elongate fingers. The resilient lattice structure can flex into a cup-shape when in pressed contact with tissues, organs or other structures within a body.

In accordance with yet further aspects of the present invention, the expanded configuration can occur in the absence of an external force applied to the first elongate finger and the second elongate finger. In the expanded configuration, the first distal end and the second distal end can be separated by a gap distance of a first dimension. The collapsed configuration can occur when an external force is applied to push the first elongate finger toward the second elongate finger causing the gap distance to decrease to a gap distance of a second dimension of a smaller magnitude than the first dimension. When the retractor is in the collapsed configuration with an external force applied thereto, the resilient lattice structure can be elastically deformed. When the external force is removed from the retractor in the collapsed configuration, the spring force energy stored in the resilient lattice structure can cause the retractor to return to the expanded configuration.

In accordance with yet further aspects of the present invention, the retractor can be coupled to an actuating mechanism for manipulating the first and second elongate fingers located at a proximal end of the shaft. The actuating mechanism for manipulating the first and second elongate fingers can cause the first and second elongate fingers to move relative to each another, thereby allowing the resilient lattice structure to compliantly conform in shape to the tissues, organs or other structures.

In accordance with an example embodiment of the present invention, a method for retracting tissues, organs or other structures in a laparoscopic surgical procedure is provided. The method can include the steps of introducing a surgical retractor into a body cavity containing the tissues, organs or other structures, the retractor comprising a single continuous structure configured as a shaft that branches into a first elongate finger with a first distal end opposite the shaft, a second elongate finger with a second distal end opposite the shaft, and a resilient lattice structure disposed between the first elongate finger and the second elongate finger. The retractor can have an expanded configuration and a collapsed configuration based on relative distance between the first distal end and the second distal end. When the retractor is in the collapsed configuration, spring force energy can be stored in the resilient lattice structure. The collapsed configuration can occur when an external force is applied to push the first distal end and the second distal end toward each other. The retractor can further be coupled to an actuating mechanism for manipulating the first and second elongate fingers located at a proximal end of the shaft. The method can further include removing the external force from the retractor, causing the retractor to return to the expanded configuration. The method can also include operating the actuating mechanism, thereby allowing the resilient lattice to compliantly conform in shape to the tissues, organs or other structures.

In accordance with an example embodiment of the present invention, a kit is provided. The kit includes a surgical retractor as described above. The kit further includes a laparoscopic port suitable for use in inserting the surgical retractor into a body cavity, wherein the port comprises a flexible, elongate hollow tube suitable for passage of the surgical retractor there through.

In accordance with an example embodiment of the present invention, a surgical retractor is provided. The surgical retractor can be a single continuous structure that includes a shaft. The shaft can branch into a first elongate finger with a first distal end opposite the shaft and a second elongate finger with a second distal end opposite the shaft. The retractor can further include a resilient lattice structure disposed between the first elongate finger and the second elongate finger. The first elongate finger and the second elongate finger can have an expanded configuration and a collapsed configuration relative to each other. The expanded configuration can occur in the absence of an external force applied to the first elongate finger and the second elongate finger wherein the first distal end and the second distal end are separated by a gap distance of a first dimension. The collapsed configuration can occur when an external force is applied to push the first elongate finger and the second elongate finger toward each other causing the gap distance to decrease to a gap distance of a second dimension, the second dimension being of smaller magnitude than the first dimension. When the retractor is in the collapsed configuration with an external force applied thereto, the resilient lattice structure can be elastically deformed and stores spring energy therein. When the external force is removed from the retractor in the collapsed configuration, the spring energy stored in the resilient lattice structure can cause the retractor to return to the expanded configuration.

BRIEF DESCRIPTION OF THE FIGURES

These and other characteristics of the present invention will be more fully understood by reference to the following detailed description in conjunction with the attached drawings, in which.

DETAILED DESCRIPTION

An illustrative embodiment of the present invention relates to a surgical retractor device for retaining and/or moving internal organs during minimally invasive or laparoscopic surgery. For example, the surgical retractor can include a shaft that branches into a first elongate finger with a first distal end opposite the shaft and a second elongate finger with a second distal end opposite the shaft. In general, the elongate fingers can have the same length, thickness and substantially the same degree of compliance or flexibility. In addition, the retractor can include a resilient lattice structure disposed between the first elongate finger and the second elongate finger. The resilient lattice structure can have a diamond-shaped or similar pattern, as would be appreciated by one skilled in the art. To improve manufacturability and safety, the retractor can be a single continuous structure formed from one sheet of material. The material can be a biocompatible compliant material such as polypropylene or other material that is capable of withstanding the forces of retraction without unduly deforming but also capable of conforming to the tissues, organs and other structures within the body that it is meant to retain and/or move.

The retractor further has an expanded configuration and a collapsed configuration based on the relative distance between the first distal end and the second distal end. The collapsed configuration occurs when an external force is applied to push the first elongate finger toward the second elongate finger. In this configuration, spring force energy is stored in the resilient lattice structure. When the retractor is in the collapsed configuration, it can be inserted through a cavity into the body. When the external force is removed from the retractor, the spring force energy stored in the resilient lattice structure causes the retractor to return to the expanded configuration. In the expanded configuration, the resilient lattice structure can be used to retain and/or move internal organs.

FIGS. 1A through 8, wherein like parts are designated by like reference numerals throughout, illustrate an example embodiment or embodiments of a surgical retractor device for retaining and/or moving internal organs during laparoscopic or minimally invasive surgery, according to the present invention. Although the present invention will be described with reference to the example embodiment or embodiments illustrated in the figures, it should be understood that many alternative forms can embody the present invention. For example, although for purposes of clarity the example embodiments are described with reference to a surgical retractor device for use in laparoscopic or minimally invasive procedures, the present invention alternatively can be implemented in accordance with retractor devices used in other procedures. Accordingly, the present invention is not limited exclusively to surgical retractor devices, as would be appreciated by one of skill in the art upon reading the present invention. One of skill in the art will additionally appreciate different ways to alter the parameters of the embodiment(s) disclosed, such as the size, shape, or type of elements or materials, in a manner still in keeping with the spirit and scope of the present invention.

FIGS. 1A through 4B depict perspective views of a surgical retractor 10 for retaining and/or moving internal organs during laparoscopic or minimally invasive surgery, in accordance with example embodiments of the present invention. As shown in the example embodiments of FIGS. 1A through 4B, the surgical retractor 10 includes a shaft 12. In some embodiments, the shaft 12 can be hollow. Alternatively, in other embodiments, the shaft 12 can be solid. The shaft 12 is generally sized, shaped and dimensioned to allow it be inserted into a body cavity. In some embodiments, the shaft 12 may have a diameter ranging between about 1 mm and about 12 mm (about 0.04 inches and about 0.47 inches). In other embodiments, the shaft 12 may have a diameter ranging between about 1 mm and about 3 mm (about 0.04 inches and about 0.12 inches). In yet some other embodiments, the shaft 12 may have a diameter ranging between about 5 mm and about 8 mm (about 0.2 inches and about 0.3 inches). In other embodiments, the shaft 12 may have a length ranging between about 2 inches and about 24 inches. As used herein, the term "about" or "approximately" refers to a variation of 10% from the indicated values (e.g., 1 mm, 3 mm, 5 mm, 8 mm, 12 mm etc.), or in case of a range of values, means a 10% variation from both the lower and upper limits of such ranges. For instance, "about 5 mm" refers to a range of between 4.5 mm and 5.5 mm. The shaft 12 may be generally rectangular in shape (as shown in FIGS. 1A through 4B), or can have a shape generally resembling a cylinder, triangular pyramid, or any other suitable shape, as would be appreciated by those of skill in the art.

Furthermore, the shaft 12 is generally formed from a material that is sufficiently flexible to allow it to be inserted into a body cavity and navigated around tissues, organs and other structures within the body without permanent or plastic deformation, and also sufficiently rigid to allow it to maintain its structure. In some embodiments, the shaft 12 has a high elastic strain (i.e., ratio of yield strength to Young's modulus). In other embodiments, the shaft 12 has a high modulus of rigidity (i.e., yield strength squared over two (2) times the Young's modulus). In one embodiment, the material is qualified by 1000*Sy/E(yield strength to modulus ratio)>=10. In other embodiments, the material can be qualified by 1000*Sy/E(yield strength to modulus ratio) <=10. The shaft 12 is further formed from a material that is biocompatible. Examples of materials suitable for use with the present invention include, but are not limited to, certain metals and plastics such as polypropylene, titanium, metallic glass, PEEK, steel, carbon fiber, shape memory alloy, shape memory polymers, Delrin®, Kevlar®, and other composite materials. Other materials are also suitable for use with the present invention, as would be appreciated by one skilled in the art.

In addition to the shaft 12, the surgical retractor 10 of FIGS. 1A through 4B also includes two or more elongate fingers that extend from the shaft 12. In the example embodiments of FIGS. 1A through 4B, the retractor 10 includes a first elongate finger 14 with a first distal end 16 opposite the shaft 12 and a second elongate finger 18 with a second distal end 20 opposite the shaft 12. It should be noted that the term "distal" as used herein refers to the side, direction or extremity that is furthest away from the operator, which is toward the center of the patient's body. Thus, the distal extremity of the device always remains inside of the body of the patient being treated. Conversely the term "proximal" as used herein refers to the side, direction or extremity closest to the operator.

In the example embodiments of FIGS. 1A through 4B, each of the elongate fingers 14, 18 is substantially straight (e.g., non-curved). In some embodiments, the elongate fingers 14, 18 may be curved in one or more planes. In the example embodiments of FIGS. 1A through 4B, each of the elongate fingers 14, 18 are substantially the same length. In alternate embodiments, the elongate fingers 14, 18 may have different lengths. In one embodiment, the elongate fingers 14, 18 have a length ranging between about 51 mm to about 610 mm (about 2 inches to about 24 inches). In the example embodiments of FIGS. 1A through 4B, each of the elongate fingers 14, 18 are substantially the same thickness. In alternate embodiments, the elongate fingers 14, 18 may have different thicknesses. In one embodiment, each of the elongate fingers 14, 18 may have a thickness ranging between about 1 mm and about 12 mm (about 0.04 inches and about 0.47 inches). The elongate fingers 14, 18 may be generally rectangular in shape (as shown in FIGS. 1A through 4B), or can have a shape generally resembling a cylinder, triangular pyramid or other cross-sectional shape, or any other suitable shape, as would be appreciated by those of skill in the art. The elongate fingers 14, 18 can be tapered at one or both ends. In the example embodiment of FIGS. 1A through 4B, the elongate fingers 14, 18 are arranged substantially parallel to one another, as depicted.

Furthermore, the elongate fingers 14, 18 are generally formed from a material that is sufficiently flexible to allow it to be inserted into a body cavity and navigated around tissues, organs and other structures within the body without permanently or plastically deforming, and also sufficiently rigid to allow it to maintain its structure during such manipulations. In the example embodiments of FIGS. 1A through 4B, each of the elongate fingers 14, 18 have substantially the same degree of flexibility. In alternate embodiments, the elongate fingers 14, 18 may have different degrees of flexibility. In some embodiments, the elongate fingers 14, 18 are formed from a material that has a high elastic strain (i.e., ratio of yield strength to Young's modulus). In other embodiments, the elongate fingers 14, 18 are formed from a material that has a high modulus of rigidity (i.e., yield strength squared over two (2) times the Young's modulus). In one embodiment, the material is qualified by 1000*Sy/E(yield strength to modulus ratio)>=10. In other embodiments, the material can be qualified by 1000*Sy/E(yield strength to modulus ratio)<=10. The elongate fingers 14, 18 are further formed from a material that is biocompatible. Examples of materials suitable for use with the present invention include, but are not limited to, certain metals and plastics such as polypropylene, titanium, metallic glass, PEEK, steel, carbon fiber, shape memory alloy, shape memory polymers, Delrin®, Kevlar®, and other composite materials. Other biocompatible materials are also suitable for use with the present invention, as would be appreciated by one skilled in the art.

In the example embodiments of FIGS. 1A through 4B, the elongate fingers 14, 18 are continuous with the shaft 12. In such embodiments, the elongate fingers 14, 18 and the shaft 12 are formed from one piece of material, as depicted. For example, the elongate fingers 14, 18 and the shaft 12 can be formed by injection molding or other similar process, as may be appreciated by one skilled in the art. In other embodiments, the elongate fingers 14, 18 and the shaft 12 may be formed from multiple pieces. In such embodiments, the elongate fingers 14, 18 and the shaft 12 may be formed from multiple layers of materials and/or multiple components. In yet some other embodiments, the elongate fingers 14, 18 may be removably coupled with the shaft 12. In these embodiments, a fastening mechanism (e.g., screws, clips, etc.) may be used to affix the elongate fingers 14, 18 to the shaft 12. Alternatively, the elongate fingers 14, 18 can slide in and out of the fastening mechanism. Additionally and/or alternatively, the elongate fingers 14, 18 can be affixed to the shaft 12 by glue or other adhesives, staples, tacks, welding, sintering, or the like.

In addition to the shaft 12 and the elongate fingers 14, 18, the surgical retractor 10 of FIGS. 1A through 4B also includes a resilient lattice structure 22 that extends between the elongate fingers 14, 18. In general, the resilient lattice structure 22 acts as a net to retain and/or move tissues, organs and other structures within the body. To accomplish this task, the resilient lattice structure 22 may have various shapes and patterns, as may be appreciated by one skilled in the art. In the example embodiment shown in FIGS. 1A through 3, the resilient lattice structure 22 may have a diamond-shaped pattern. In an alternate embodiment shown in FIG. 4B, the resilient lattice structure 22 may have a semi-circular pattern. Of course, one skilled in the art would appreciate that other shapes and patterns would fall within the spirit and scope of the present invention.

The resilient lattice structure 22, furthermore, can be formed from a material that is sufficiently flexible to enable it to be inserted into a body cavity and navigated around tissues, organs and other structures within the body without permanently or plastically deforming, and also sufficiently rigid to allow it to maintain its structure. Additionally, the elongate fingers 14, 18 are generally formed from a material that is sufficiently compliant to allow it to form a cup-shape around the tissues, organs and other structures within the body that it is meant to retain and/or move. The phrase "compliantly conform" as utilized herein is intended to mean that the resilient lattice structure 22 forms a cup-shape when in contact with, and pressed against, tissues, organs and other structures within the body. In some embodiments, the resilient lattice structure 22 is formed from a material that has a high elastic strain (i.e., ratio of yield strength to Young's modulus). In other embodiments, the resilient lattice structure 22 is formed from a material that has a high modulus of rigidity (i.e., yield strength squared over two (2) times the Young's modulus). In one embodiment, the material is qualified by 1000*Sy/E(yield strength to modulus ratio)>=10. In other embodiments, the material can be qualified by 1000*Sy/E(yield strength to modulus ratio) <=10. In an embodiment, the resilient lattice structure 22 is further formed from a material that is biocompatible. Examples of materials suitable for use with the present invention include, but are not limited to, certain metals and plastics such as polypropylene, titanium, metallic glass, PEEK, steel, carbon fiber, shape memory alloy, shape memory polymers, Delrin®, Kevlar®, and other composite materials. Other biocompatible materials are also suitable for use with the present invention, as would be appreciated by one skilled in the art.

In the example embodiments of FIGS. 1A through 4B, the resilient lattice structure 22 is continuous with the elongate fingers 14, 18. In such embodiments, the resilient lattice structure 22 and the elongate fingers 14, 18 are formed from one piece of material. For example, the resilient lattice structure 22 and the elongate fingers 14, 18 can be formed by injection molding or other similar process, as may be appreciated by one skilled in the art. In other embodiments, the resilient lattice structure 22 and the elongate fingers 14, 18 may be formed from multiple pieces of materials. In these embodiments, the resilient lattice structure 22 and the elongate fingers 14, 18 may be formed from multiple layers of materials and/or multiple components. In yet some other embodiments, the resilient lattice structure 22 may be removably coupled to the elongate fingers 14, 18. In these embodiments, a fastening mechanism (e.g., screws, clips, etc.) may be used to affix the resilient lattice structure 22 to the elongate fingers 14, 18. Alternatively, the resilient lattice structure 22 can be affixed to the elongate fingers 14, 18 by glue or other adhesives, staples, tacks, welding, sintering, or the like.

To retain and/or move tissues, organs and other structures within the body during laparoscopic or minimally invasive surgery, the surgical retractor 10 has multiple configurations. In one embodiment, the surgical retractor 10 has an expanded configuration and a collapsed configuration based on relative distance between the first distal end 16 and the second distal end 20. In the example embodiments shown in FIGS. 1A through 4B, the retractor 10 is in an expanded configuration where the elongate fingers 14, 18 are separated and distal from one another. The expanded configuration occurs in the absence of an external force applied to the elongate fingers 14, 18. In an expanded configuration, the first distal end 16 and the second distal end 20 are separated by a gap distance of a first dimension 24. In an expanded configuration, the retractor 10 may have varying degrees of angle between the elongate fingers 14, 18. In a fully expanded configuration, the retractor 10 may have an angle of up to 180 degrees between the elongate fingers 14, 18. In the example embodiment shown in FIG. 1A, the resilient lattice structure 22 has a 90 degree angle 28 between the elongate fingers 14, 18. In the example embodiment shown in FIGS. 2A and 2B, the resilient lattice structure 22 has a 45 degree angle 30 between the elongate fingers 14, 18. In the example embodiment shown in FIG. 3, the resilient lattice structure 22 has a 12 degree angle 32 between the elongate fingers 14, 18. Of course, one skilled in the art would appreciate that other angles between the elongate fingers 14, 18 would fall within the spirit and scope of the present invention. It should be appreciated that the example embodiments shown in FIGS. 1A through 3 can depict the retractor 10 in both a fully expanded or partially expanded configuration.

Figure 1A:
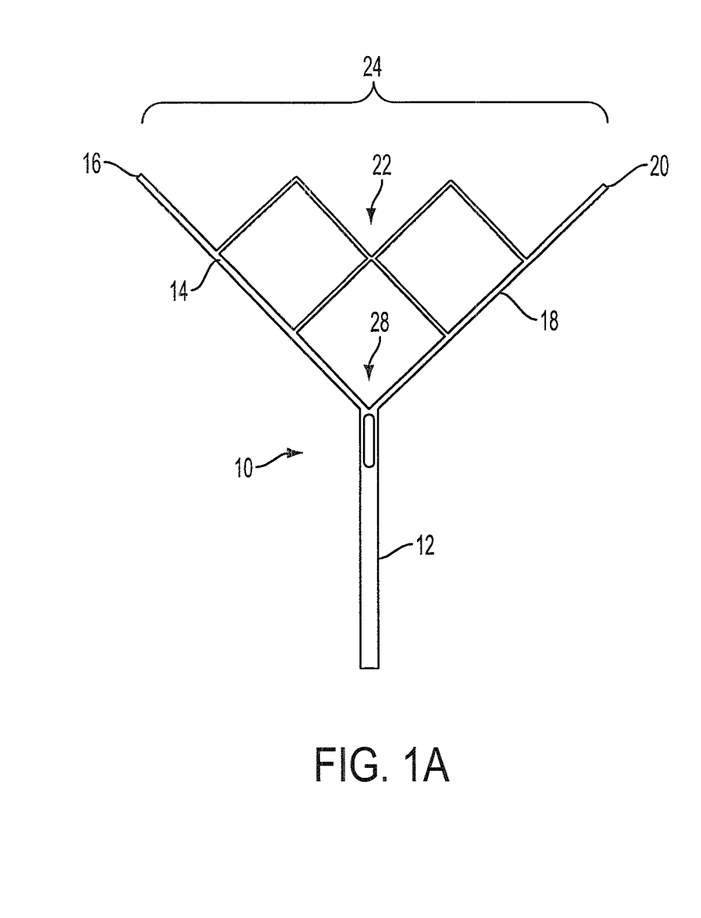
FIG. 1A and FIG. 1B are perspective views of a surgical retractor according to an example embodiment of the present invention.
Figure 1B:
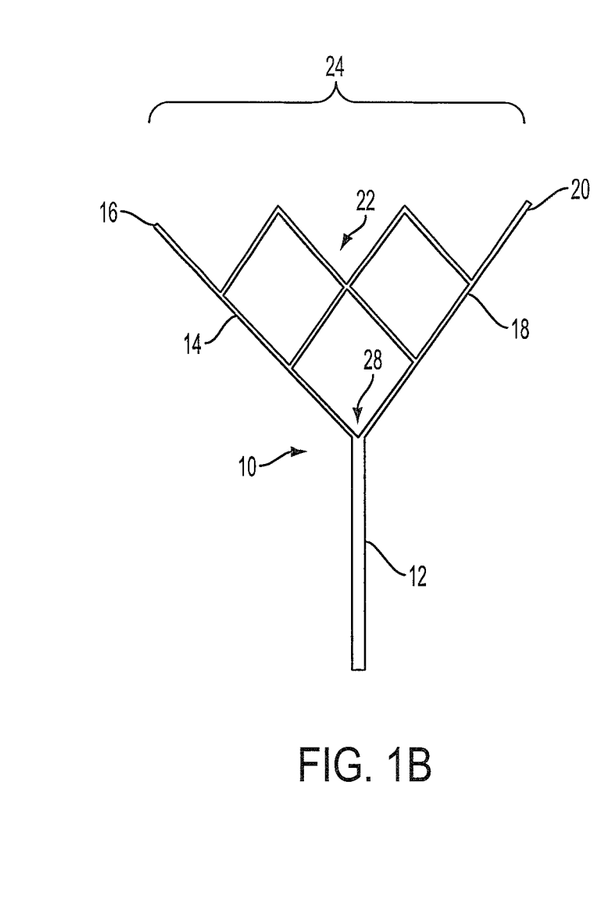
Figure 2A:
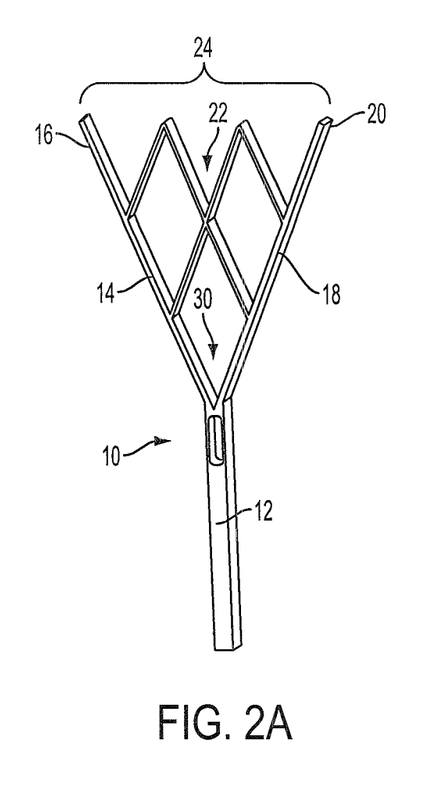
FIG. 2A and FIG. 2B are perspective views of a surgical retractor according to an example embodiment of the present invention.
Figure 2B:
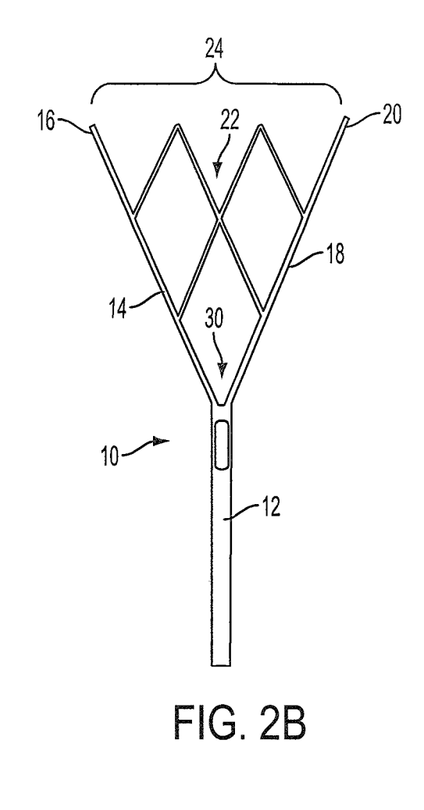
Figure 3:
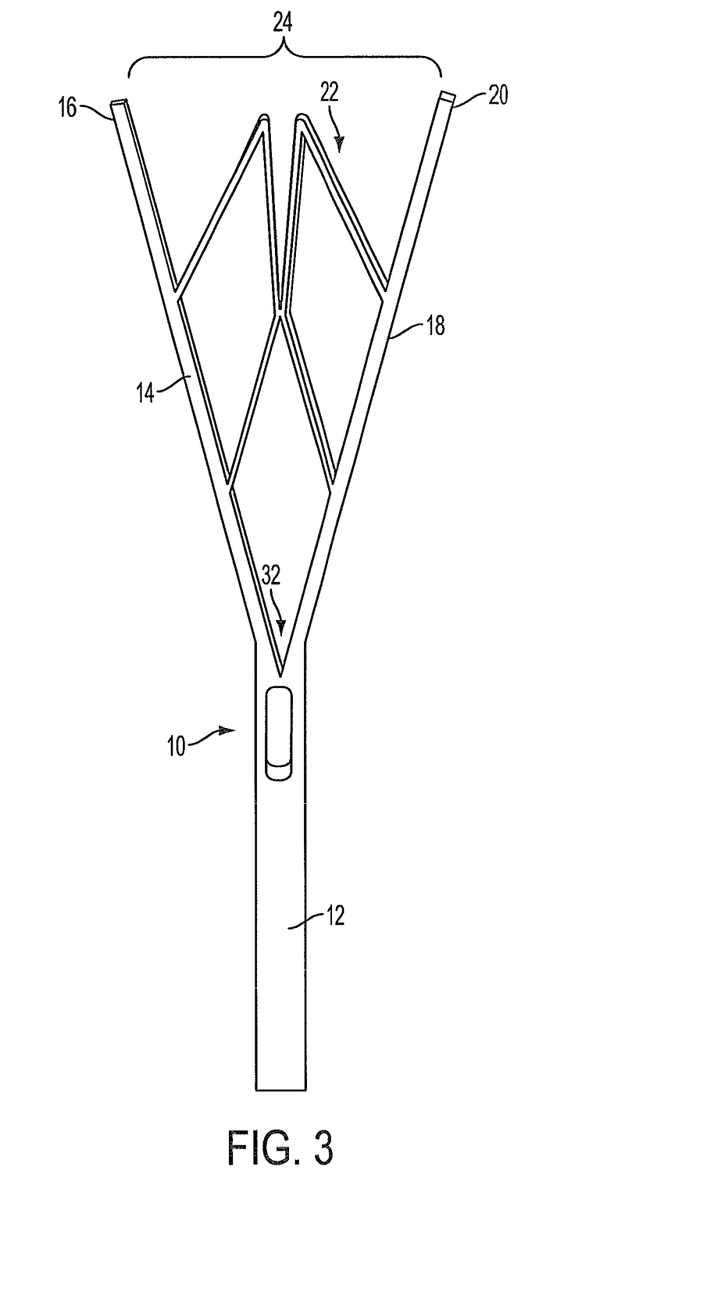
FIG. 3 is a perspective view of a surgical retractor according to an example embodiment of the present invention.
Figure 4A:
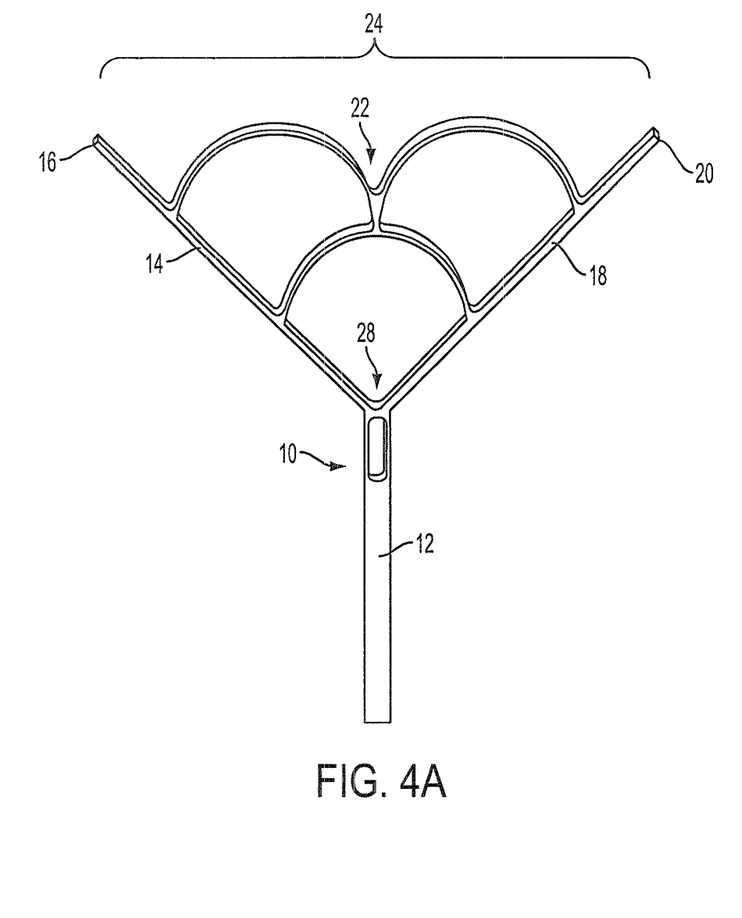
FIG. 4A and FIG. 4B are perspective views of a surgical retractor according to an example embodiment of the present invention.
Figure 4B:
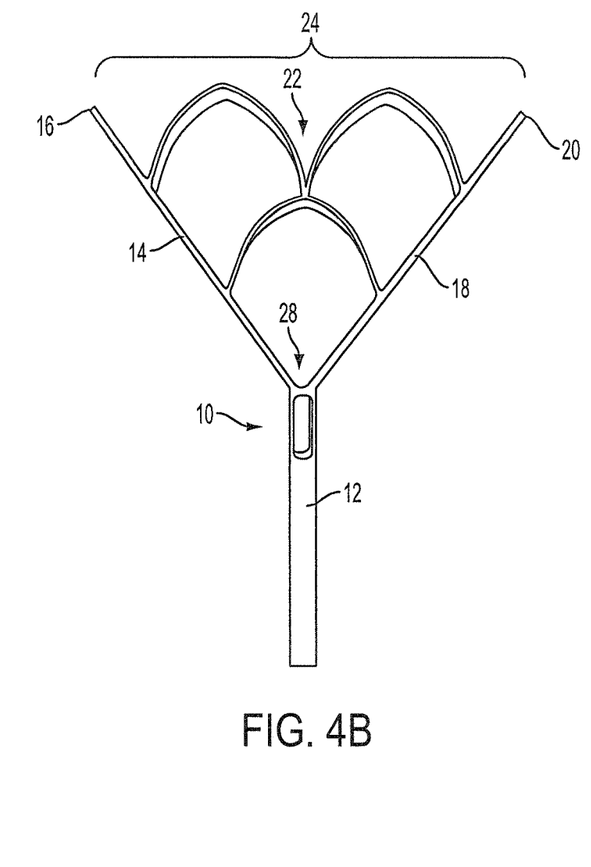
Figure 5A:
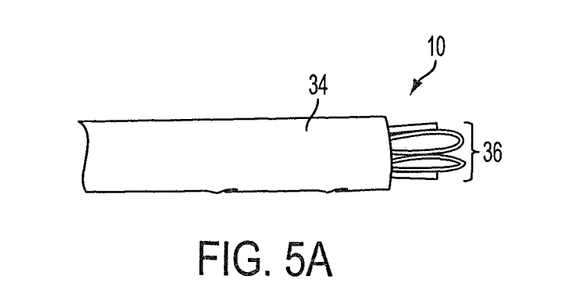
FIGS. 5A, 5B, and 5C are perspective views of various progressive stages of a surgical retractor being actuated in and out of a tube.

In another embodiment, the retractor 10 may be in a collapsed configuration where the elongate fingers 14, 18 are in mutual contact or near mutual contact with one another, as shown in FIG. 5A. In the collapsed configuration, the angle between the elongate fingers 14, 18 is substantially zero, or when the elongate fingers 14, 18 are generally in a parallel orientation relative to each other along a majority of their length (such as when the retractor 10 is sliding through a tubular cannula, compressing the retractor 10 into the collapsed configuration, as depicted in FIG. 5A. The collapsed configuration occurs when an external force is applied to push the first elongate finger 14 toward the second elongate finger 18 or, alternatively, the second elongate finger 18 toward the first elongate finger 14, causing the gap distance to decrease to a gap distance of a second dimension 36. In a collapsed configuration, the second dimension 36 may be of a smaller magnitude than the first dimension 24. Stated differently, in a collapsed configuration, the elongate fingers 14, 18 are in mutual contact or near mutual contact with one another. When an external force applied thereto and the retractor 10 is in the collapsed configuration with (i.e., when the elongate fingers 14, 18 are in mutual contact or near mutual contact with one another), the resilient lattice structure 22 is elastically deformed. Furthermore, when the retractor is in the collapsed configuration, spring force energy may be stored in the resilient lattice structure 22, which can cause the resilient lattice structure 22 to expand upon removal of the external force, and return to an expanded configuration. Alternatively, it may be possible that no spring force energy is stored in the resilient lattice structure 22 due to material properties and/or the resilient lattice structure configuration. In such circumstances, a separate device can be used to open and close the retractor 10.

Figure 5B:
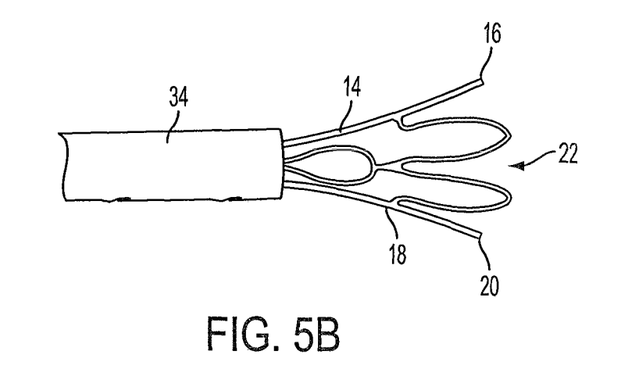
Figure 5C:
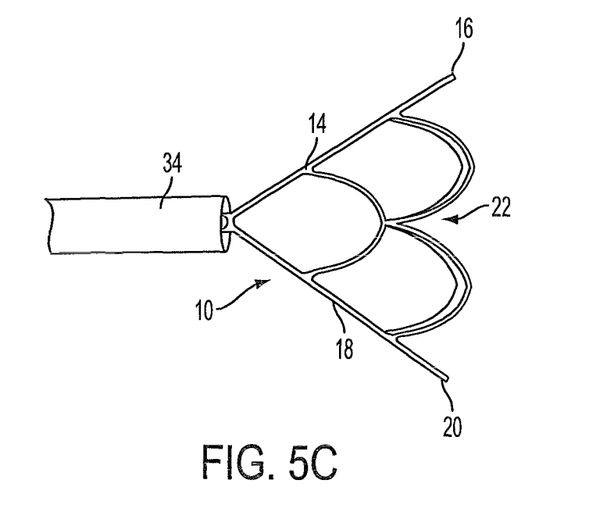

When the external force is removed from the retractor 10 in the collapsed configuration, the spring force energy stored in the resilient lattice structure 22 causes the retractor 10 to return to the expanded configuration. The transition of the retractor 10 from a collapsed configuration to an expanded configuration is depicted in FIGS. 5A through 5C. As shown in FIG. 5A, the retractor 10 is in a collapsed configuration with the elongate fingers 14, 18 in mutual contact or near mutual contact with one another. In this collapsed configuration, the retractor 10 may be introduced into a body cavity though a tube 34. Once the retractor 10 is at the location of interest within the body, the retractor 10 may begin to expand. FIG. 5B shows the retractor 10 in a partially-opened configuration. Depending on the size of the organ or structure to be retained and/or moved, the retractor 10 may be locked in a partially-opened configuration. This partially-opened configuration may be beneficial if a small-sized organ is being retracted. If, for example, a larger-sized organ is being retracted, the retractor 10 may be opened to a fully expanded configuration as shown in FIG. 5C.

Figure 6:
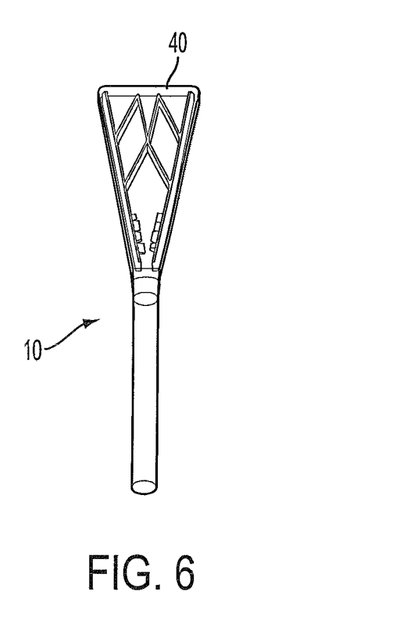
FIG. 6 is a perspective view of a surgical retractor according to an example embodiment of the present invention.

The surgical retractor 10 of the present invention may be uncoated or may include a coating. The coating may be any suitable coating, including as a non-limiting example, a biodegradable or bioabsorbable coating capable of carrying and delivering a therapeutic agent, and/or providing an increased degree of lubricity, as desired. Such a coating can be applied to the retractor 10 with sufficient thickness to serve as, e.g., a physical protective layer between surrounding tissue and the surface of the retractor 10. The coating can also help prevent contamination of the inner portions of the retractor 10. Alternatively and/or additionally, the retractor 10 can have a covering 40 disposed around its exterior to prevent contamination of the inner portions of the retractor 10 as shown in FIG. 6. The covering 40 can be easily removed and disposed prior to use of the retractor 10.

Figure 7:
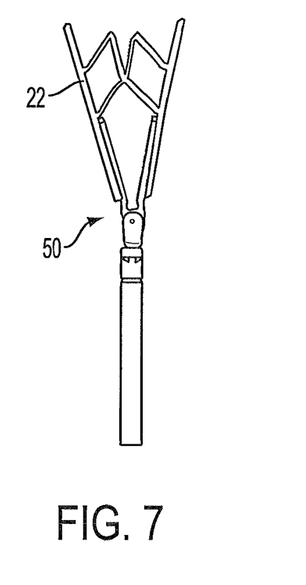
FIG. 7 is a perspective view of a surgical retractor according to an example embodiment of the present invention.
Figure 8:
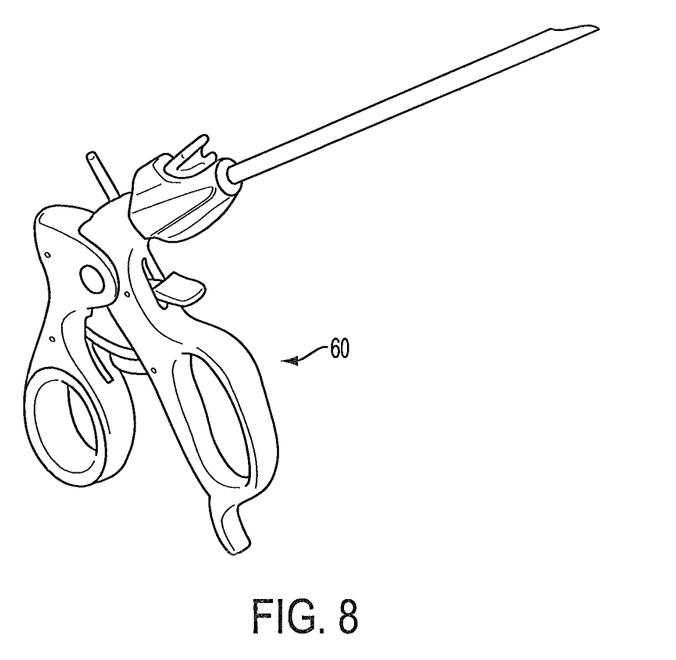
FIG. 8 is an actuation mechanism for manipulating the surgical retractor according to an example embodiment of the present invention.

The surgical retractor 10 of the present invention may further be retrofitted to existing retractor devices. For example, the resilient lattice structure 22 may be attached to other retractor devices 50 as shown in FIG. 7. One such existing retractor device is Intuitive Surgical's DaVinci robot retractor. In this manner, the retractor 10 of the present invention can be used in a variety of surgical applications such as robotic laparoscopic surgery.

The retractor 10 may further be coupled to an actuation mechanism for manipulating elongate fingers 14, 18 located at a proximal end of the shaft 12. Such mechanisms allow the operator to control the degree of opening of the elongate fingers 14, 18 with a high degree of precision. The actuation mechanism causes the elongate fingers 14, 18 to move relative to each another, thereby allowing the resilient lattice structure 22 to compliantly conform in shape to the tissues, organs or other structures with the body. In the example embodiment shown in FIG. 8, the actuation mechanism for manipulating the elongate fingers 14, 18 is a scissor-like unit 60. Of course, it should be appreciated that other actuation mechanisms may also fall within the scope of the present invention.

The retractor 10 may further be coupled to an anchor for anchoring and/or securing the retractor 10 to the tissues, organs or other structures within a body. The anchor may prevent the accidental removal of the retractor 10 or the tissues, organs or other structures it is holding from the body. The anchor may also prevent movement of the retractor 10 or the tissues, organs or other structures it is holding within the body. Examples of anchors that are capable of being used to anchor and/or secure the retractor 10 to the tissues, organs or other structures include, but are not limited to, hooks, pins, clasps, cables and other similar devices.

In operation, the surgical retractor 10 can be used in laparoscopic or minimally invasive surgery to retain and/or move internal tissues, organs and other structures, as would be appreciated by one of skill in the art upon reading the present specification. First, the surgical retractor 10 is introduced into a body cavity through a tube or trocar and is advanced to the site containing the tissues, organs and other structures. Once at the site of interest, the user can manipulate the elongate fingers 14, 18 using an actuation mechanism. For example, by manipulating the actuation mechanism, the external force may be removed from the retractor 10, causing the retractor 10 to return to an expanded configuration. The user can then operate the actuation mechanism in such a way to allow the resilient lattice structure 22 to compliantly conform in shape to the tissues, organs or other structures in the body and to retain and/or move the tissues, organs or other structures. Once adequately positioned, the retractor 10 may be secured in place by an anchor. Once the procedure is completed, the retractor may be detached and/or removed by first unlocking the anchor and then manipulating the actuation mechanism in such a way that the resilient lattice structure 22 releases or un-cups the tissues, organs or other structures and then the retractor 10 transitions to a collapsed configuration. Once in the collapsed configuration, the retractor 10 may be pulled through the tube or trocar and removed from the body.

The surgical retractor of the present invention may be distributed as a kit. The kit may include a surgical retractor according to any of the embodiments discussed herein and a laparoscopic port suitable for use in inserting the surgical retractor into a body cavity. The port can be formed from a flexible material to allow it to navigate through the body and around various tissues, organs or other structures within the body. In addition, the port can be hollow to allow passage of the surgical retractor there through.

Notably, the surgical retractor 10 of the present invention provides a user with superior grip on organs due to the ability of the resilient lattice structure 22 to deform into a more cup-like shape. The retractor 10 also offers superior manufacturability in that it is capable of being manufactured from one single piece of material, for example by machining a solid block of material into the desired surgical retractor 10 shape, or as a single piece of material, such as by injection molding or 3D printing, rather than from multiple pieces. By being manufactured from or as a single piece of material, the retractor 10 provides the added safety benefit of the retractor 10 remaining intact during a surgical procedure without the risk of separate pieces that could loosen or break, thereby reducing the likelihood that pieces or sections of the retractor 10 will fall off during surgery. Furthermore, manufacturing the retractor 10 from a single piece of material rather than from multiple components will improve sterilization of the retractor 10, thus reducing the likelihood that the retractor 10 may be contaminated during use.

In addition, in accordance with embodiments of the present invention, the retractor 10 may be retrofitted to existing devices. This reduces the need for manufacturing additional complex or expensive parts. The retractor 10 can also function as a clamping retractor if the two fingers are brought together with enough force to grip an organ. This added capability reduces the need for purchasing and using multiple devices. Upon reading the present specification, one of skill in the art will appreciate yet further benefits not described herein.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A surgical retractor, comprising:
    a single continuous structure configured as a shaft that branches into a first elongate finger with a first free distal end opposite the shaft, a second elongate finger with a second free distal end opposite the shaft, and a resilient lattice structure disposed between the first elongate finger and the second elongate finger;
    wherein the retractor has an expanded configuration and a collapsed configuration based on a relative distance between the first free distal end and the second free distal end; and
    wherein when the retractor is in the collapsed configuration, spring force energy is stored in the resilient lattice structure.

2. The surgical retractor according to claim 1, wherein the shaft has a diameter ranging from about 1 mm to about 12 mm (about 0.04 inches and about 0.47 inches) and a length ranging from about 2 inches to about 24 inches.

3. The surgical retractor according to claim 1, wherein the retractor is formed from a biocompatible material.

4. The surgical retractor according to claim 1, wherein each of the first and second elongate fingers is straight.

5. The surgical retractor according to claim 1, wherein the first and second elongate fingers are in the collapsed configuration when the retractor is introduced into a body cavity.

6. The surgical retractor according to claim 1, wherein the first and second elongate fingers have substantially the same degree of flexibility.

7. The surgical retractor according to claim 1, wherein the resilient lattice structure is folded when the retractor is introduced into a body cavity.

8. The surgical retractor according to claim 1, wherein the resilient lattice structure comprises a diamond-shaped pattern or a semi-circular pattern.

9. The surgical retractor according to claim 1, wherein the retractor forms an angle between 0 degrees and 90 degrees between the first and second elongate fingers.

10. The surgical retractor according to claim 1, wherein the resilient lattice structure flexes into a cup-shape when pressed in contact with tissues, organs or other structures within a body.

11. The surgical retractor according to claim 1, wherein the expanded configuration occurs in the absence of an external force applied to the first elongate finger and the second elongate finger.

12. The surgical retractor according to claim 11, wherein in the expanded configuration, the first free distal end and the second free distal end are separated by a gap distance of a first dimension.

13. The surgical retractor according to claim 12, wherein the collapsed configuration occurs when an external force is applied to push the first elongate finger toward the second elongate finger causing the gap distance to decrease to a gap distance of a second dimension of a smaller magnitude than the first dimension.

14. The surgical retractor according to claim 1, wherein when the retractor is in the collapsed configuration with an external force applied thereto, the resilient lattice structure is elastically deformed.

15. The surgical retractor according to claim 14, wherein when the external force is removed from the retractor in the collapsed configuration, the spring force energy stored in the resilient lattice structure causes the retractor to return to the expanded configuration.

16. The surgical retractor according to claim 1, wherein the retractor is coupled to an actuating mechanism for manipulating the first and second elongate fingers located at a proximal end of the shaft.

17. The surgical retractor according to claim 16, wherein the actuating mechanism for manipulating the first and second elongate fingers causes the first and second elongate fingers to move relative to each another, thereby allowing the resilient lattice structure to compliantly conform in shape to tissues, organs or other structures.

18. A kit comprising:
    a surgical retractor according to claim 1; and
    a laparoscopic port suitable for use in inserting the surgical retractor into a body cavity, wherein the port comprises a flexible, elongate hollow tube suitable for passage of the surgical retractor there through.

19. The surgical retractor according to claim 1, wherein the first free distal end and the second free distal end are terminal ends that are separated from one another creating a gap between the first free distal end and the second free distal end.

20. A method for retracting tissues, organs or other structures in a laparoscopic surgical procedure, the method comprising the steps of:
- a) introducing a surgical retractor into a body cavity containing the tissues, organs or other structures, the retractor comprising:
  - (i) a single continuous structure configured as a shaft that branches into a first elongate finger with a first free distal end opposite the shaft, a second elongate finger with a second free distal end opposite the shaft, and a resilient lattice structure disposed between the first elongate finger and the second elongate finger,
    - wherein the retractor has an expanded configuration and a collapsed configuration based on relative distance between the first free distal end and the second free distal end;
    - wherein when the retractor is in the collapsed configuration, spring force energy is stored in the resilient lattice structure;
    - wherein the collapsed configuration occurs when an external force is applied to push the first free distal end and the second free distal end toward each other; and
    - wherein the retractor is coupled to an actuating mechanism for manipulating the first and second elongate fingers located at a proximal end of the shaft;
- b) removing the external force from the retractor, causing the retractor to return to the expanded configuration; and
- c) operating the actuating mechanism, thereby allowing the resilient lattice to compliantly conform in shape to the tissues, organs or other structures.

21. A surgical retractor, comprising:
- a single continuous structure configured as a shaft that branches into a first elongate finger with a first free distal end opposite the shaft, a second elongate finger with a second free distal end opposite the shaft, and a resilient lattice structure disposed between the first elongate finger and the second elongate finger;
- the first elongate finger and the second elongate finger having an expanded configuration and a collapsed configuration relative to each other, the expanded configuration occurring in the absence of an external force applied to the first elongate finger and the second elongate finger wherein the first free distal end and the second free distal end are separated by a gap distance of a first dimension, and the collapsed configuration occurring when an external force is applied to push the first elongate finger and the second elongate finger toward each other causing the gap distance to decrease to a gap distance of a second dimension, the second dimension being of smaller magnitude than the first dimension;
- wherein when the retractor is in the collapsed configuration with an external force applied thereto, the resilient lattice structure is elastically deformed and stores spring energy therein; and
- wherein when the external force is removed from the retractor in the collapsed configuration, the spring energy stored in the resilient lattice structure causes the retractor to return to the expanded configuration.

\* \* \* \* \*